(12) United States Patent
Linck

(10) Patent No.: US 9,649,132 B1
(45) Date of Patent: May 16, 2017

(54) BONE DISTRACTOR

(71) Applicant: Donald W. Linck, Pleasant Hill, CA (US)

(72) Inventor: Donald W. Linck, Pleasant Hill, CA (US)

( * ) Notice: Subject to any disclaimer, the term of this patent is extended or adjusted under 35 U.S.C. 154(b) by 91 days.

(21) Appl. No.: 14/690,796

(22) Filed: Apr. 20, 2015

(51) Int. Cl.
*A61B 17/66* (2006.01)

(52) U.S. Cl.
CPC .................. *A61B 17/663* (2013.01)

(58) Field of Classification Search
CPC ............ A61B 17/7013; A61B 17/7014; A61B 17/7019; A61B 17/702; A61B 17/7025; A61B 17/7026; A61B 17/7028; A61B 17/7029; A61B 17/7031; A61B 17/60; A61B 2017/606; A61B 17/66; A61B 17/663; A61B 17/666; A61B 2017/681; A61B 17/8004; A61B 17/8071
See application file for complete search history.

(56) References Cited

U.S. PATENT DOCUMENTS

| | | | |
|---|---|---|---|
| 6,001,096 A | 12/1999 | Bissinger et al. | |
| 6,908,469 B2 | 6/2005 | Sellers et al. | |
| 6,972,020 B1 * | 12/2005 | Grayson | A61B 17/663 606/90 |
| 7,195,481 B1 | 3/2007 | Linck | |
| 7,717,941 B2 * | 5/2010 | Petit | A61B 17/7028 606/254 |
| 7,771,434 B2 | 8/2010 | Johnston | |
| 7,892,241 B2 | 2/2011 | Ahmad et al. | |
| 7,933,862 B2 | 4/2011 | Chamberlain et al. | |
| 8,088,149 B2 * | 1/2012 | White | A61B 17/7005 606/258 |
| 8,979,858 B2 | 3/2015 | Gordon et al. | |
| 9,055,976 B2 * | 6/2015 | Li | A61B 17/663 |
| 2009/0326582 A1 * | 12/2009 | Songer | A61B 17/702 606/255 |
| 2011/0125162 A1 * | 5/2011 | Noon | A61B 17/663 606/105 |
| 2012/0239035 A1 * | 9/2012 | Li | A61B 17/663 606/57 |

* cited by examiner

*Primary Examiner* — Lynnsy Summitt
*Assistant Examiner* — Lynnsy Schneider
(74) *Attorney, Agent, or Firm* — Walter A. Rodgers

(57) ABSTRACT

A bone distractor to create separation between bone segments by means of a pair of mounts respectively secured to the bone segments and interconnected by means of a drive spring which is secured to one of the mounts and threadedly interconnected to the other mount such that rotation of the drive spring creates sufficient separation of the bone segments to allow for osteogenesis to occur.

4 Claims, 3 Drawing Sheets

BONE DISTRACTOR

BACKGROUND OF THE INVENTION

Bone distractors are utilized in the field of orthodontics in connection with the repair and regeneration of craniofacial bones and in particular the mandible and maxilla. Typically, a bone is cut or fractured to create two separate segments which results in a space formed therebetween. Through the process of osteogenesis, the regeneration of bone occurs in the space between the two segments. The distance between the bone segments can be increased over time allowing additional new growth to occur.

One means of accomplishing distraction is to affix mounts, respectively, on the two bone segments. A drive screw is threadedly interconnected to one of the mounts and is affixed to the other mount whereby rotation of the drive screw causes separation of the bone segments. Typically, distractor drive screws are somewhat inflexible such that they are not able to bend to the degree desired in many applications and sometimes break when they are bent too far.

BRIEF SUMMARY OF THE INVENTION

According to this invention, a bone distractor is utilized to create space between two bone segments so as to achieve bone growth between the segments through the process of osteogenesis. The distractor includes a pair of mounts secured, respectively, to the bone segments with a drive spring extending through one of the segments and being threadedly interconnected to the other segment. The drive spring is disposed in a holder which is integrally joined to the first mount and the drive spring extends through the second mount. The end of the drive spring extending outwardly from the first mount is attached to a round flexible activation shaft by means of a universal mount. The activation shaft is manually rotated causing rotation of the drive spring and separation of the bone segments resulting from the threaded interconnection of the drive spring and a threaded block incorporated into the second mount.

DETAILED DESCRIPTION OF THE INVENTION

Figure 1:
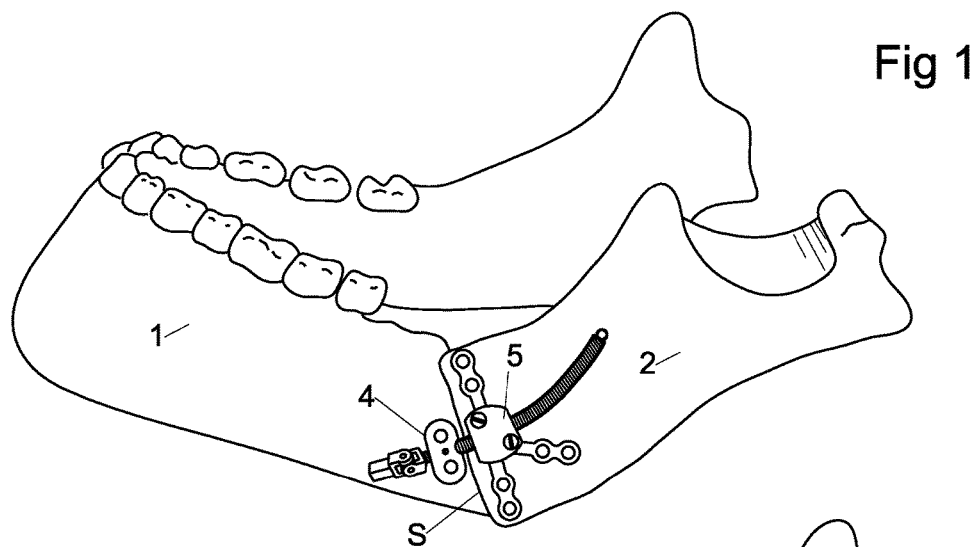
FIG. 1 is a perspective view showing the distractor before distraction has occurred.
Figure 2:
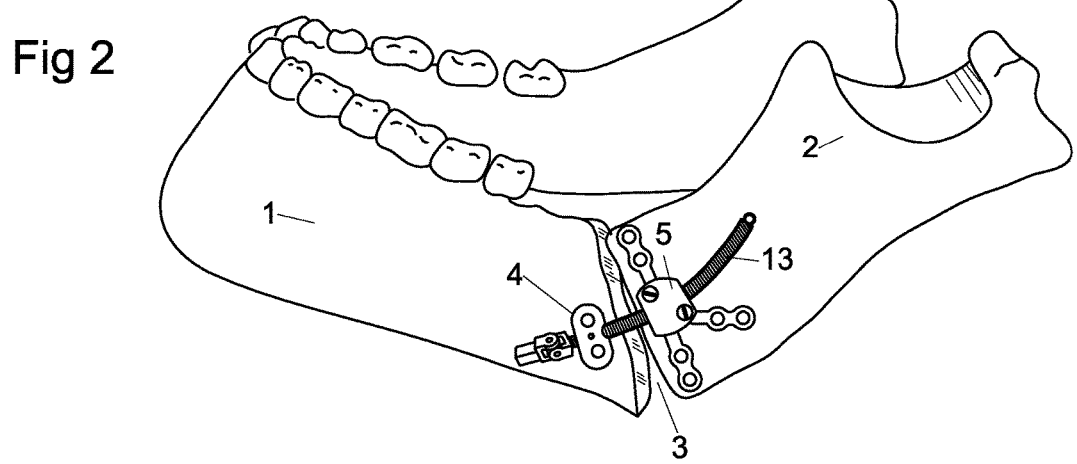
FIG. 2 is a perspective view showing the distractor after distraction has occurred.

The purpose of the bone distractor, according to this invention, is depicted in FIGS. 1 and 2 wherein, in FIG. 1, bone segments 1 and 2 are in abutting relation along severance line S. Activation of the bone distractor causes bone segments 1 and 2 to separate along the severance line into the positions shown in FIG. 2 whereby space 3 is formed therebetween.

Figure 3:
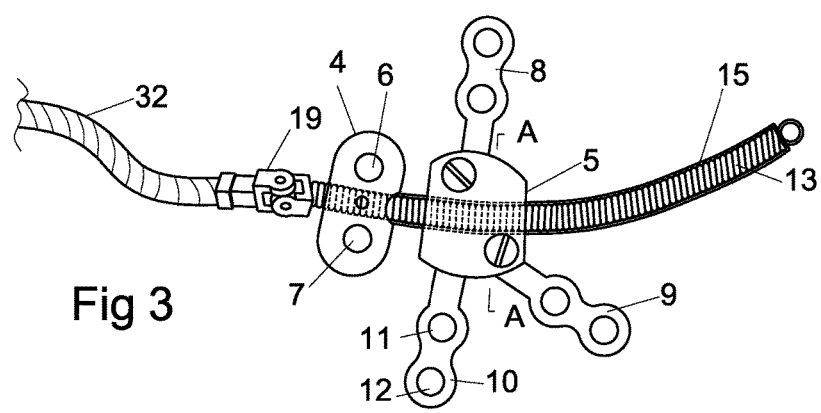
FIG. 3 is an enlarged view of the distractor device.
Figure 4:
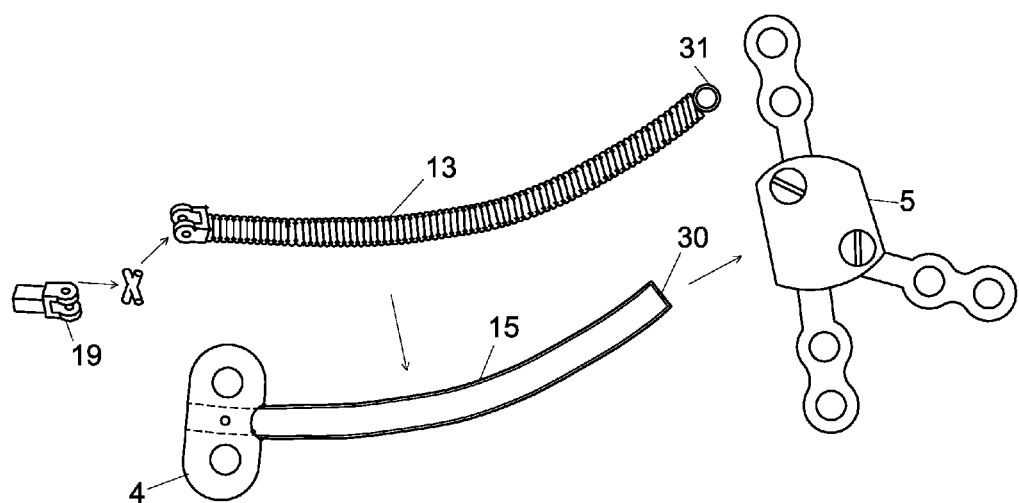
FIG. 4 is an exploded view showing individual elements of the distractor.

The distractor, as shown in FIG. 3, includes mounts 4 and 5. Mount 4 is affixed to the patient's bone by inserting bone screws through apertures 6 and 7. Similarly, mount 5 is affixed to the patient's bone by means of attachment arms 8, 9 and 10 each of which has a pair of apertures 11 and 12 formed therein. Mount 5 is secured to the patient's bone by inserting bone screws through apertures 11 and 12 of each arm 8, 9 and 10, as is well known in the art.

Figure 5:
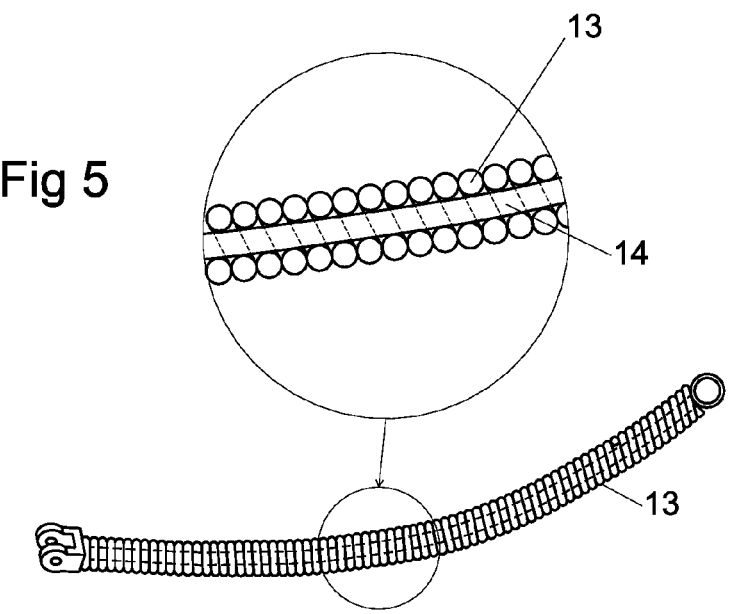
FIG. 5 is a view showing details of the drive spring.

For the purpose of activating the distractor and separating bone segments 1 and 2, round helical drive spring 13 is provided with flexible wire 14 extending substantially the entire internal length of drive spring 13, as best shown in FIG. 5. Typical drive screws known in the art are somewhat inflexible and tend to break during use. Wire 14 enhances the stabilization properties of an inherently unstable helical drive spring 13 and aids in lessening the drive screw spring back reaction after the distractor is activated.

In order to complete the bone distractor, according to this invention, drive spring 13 is disposed in trough-shaped holder 15. Holder 15 is curved and comprises bottom 16 with parallel spaced sidewalls 17 and 18 extending upwardly therefrom with the top of drive spring 13 in general alignment with the tops of sidewalls 17 and 18. As best shown in FIG. 3, the proximate end of holder 15 is integrally joined to mount 4 with drive spring 13 extending through an elongated channel formed in mount 4 and with universal joint 19 affixed to the exposed free end of drive spring 13.

Figure 6:
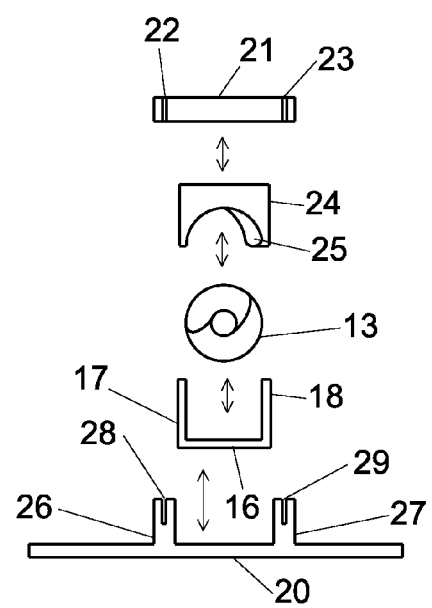
FIG. 6 is an exploded sectional view taken along the line A-A in FIG. 3.

As shown in FIG. 6, mount 5 contains multiple elements including base plate 20 and top plate 21 with apertures 22 and 23 formed in top plate 21. Block 24 is secured to the underside of top plate 21 by any suitable means such as a screw threaded through an aperture formed in top plate 21 and into block 24. The lower inner surface of block 24 includes threads 25.

The assembly of mount 5 is completed by attaching top plate 21 to base plate 20 by placing top plate 21 on upstanding supports 26 and 27 which in turn are integrally joined to base plate 20. Top plate 21 is secured in place by means of screws inserted through apertures 22 and 23 formed in top plate 21 and into threaded apertures 28 and 29 formed, respectively, in supports 26 and 27 in such manner that threaded block 24 is situated between sidewalls 17 and 18.

Simultaneously with this operation, holder 15 with drive spring 13 disposed therein is positioned on base plate 20 between supports 26 and 27 and block 24 is seated between sidewalls 17 and 18 so that threaded portion 25 is threadedly interconnected with drive spring 13. In order to secure drive spring 13 in place in holder 15, the end of drive spring 13 extends through aperture 30 formed in the end of holder 15 with ring 31 formed on the end of drive spring 13 to prevent the withdrawal of drive spring 13 through aperture 30.

Following this, the bone distractor is in condition for attachment a patient's bone, as shown in FIG. 1, whereby mount 4 is attached to bone segment 1 and mount 5 is attached to bone segment 2 by means of the associated bone screws. To achieve bone distraction, flexible activation shaft 32 is releasably coupled to universal joint 19 and an appropriate drive tool is attached to the free end of activation shaft 32. Activation shaft 32 is then manipulated to cause rotation of drive spring 13. Separation of segments 1 and 2 occurs due to a combination of the threaded interconnection between drive spring 13 and threads 25 of block 24 secured to mount 5 and the integral connection of the end of holder 15 to mount 4.

The invention claimed is:

1. A bone distractor for creating a space between two bone segments comprising a pair of mounts adapted for attachment respectively to said bone segments,
   a drive spring interconnecting said mounts,
   said drive spring being helical and flexible in configuration,
   a wire disposed internally of said drive spring and being substantially co-extensive therewith,
   said drive spring being disposed in an elongated holder and said holder having an open top and an end,
   said end of said said holder being secured to one of said mounts,
   a channel formed in said one mount and said drive spring extending through said channel,
   the other of said mounts comprising a top plate and a base plate spaced apart and interconnected by means of a pair of spaced supports,
   a block being attached to the underside of said top plate, said block having a lower exposed surface and said lower surface being threaded,
   said block being partially disposed in said elongated holder,
   said holder disposed between said supports, and
   the outer surface of said drive spring threadedly interconnected to said threaded lower surface of said block.

2. The bone distractor according to claim 1 wherein said drive spring is interconnected to said one of said mounts and threadedly interconnected to the other of said mounts.

3. The bone distractor according to claim 1 wherein said drive spring comprises an end adjacent said one mount and an activation shaft is interconnected to said end by means of a universal joint.

4. The bone distractor according to claim 3 wherein said activation shaft is flexible.

* * * * *